United States Patent [19]

VanRheenen

[11] 4,416,821
[45] Nov. 22, 1983

[54] PROCESS FOR PREPARING 16-METHYLENE STEROIDS

[75] Inventor: Verlan H. VanRheenen, Portage, Mich.

[73] Assignee: The Upjohn Company, Kalamazoo, Mich.

[21] Appl. No.: 349,490

[22] Filed: Feb. 17, 1982

[51] Int. Cl.³ ............................................. C07J 7/00
[52] U.S. Cl. ..................... 260/397.1; 260/239.55 R; 260/397.3; 260/397.4; 260/397.45
[58] Field of Search ............... 260/397.3, 397.4, 397.45

[56] References Cited

U.S. PATENT DOCUMENTS

| | | | |
|---|---|---|---|
| 3,275,666 | 9/1966 | Siegmann et al. | 260/397.5 |
| 3,300,521 | 1/1967 | Anner | 260/397.4 |
| 3,641,069 | 2/1972 | Anner | 260/397.45 |
| 3,704,253 | 11/1972 | Stein | 260/397.4 |

FOREIGN PATENT DOCUMENTS 19495  2/1981  Hungary ........................ 260/397.3

OTHER PUBLICATIONS

Gazetter Chim. Ital. 91, 672, (1961). P. de Ruggieri et al. "Steroidi 16-metel-androstani" (See pp. 562 and 678).
Tetrahedron Letters 39, 3753 (1978), Y. Ueno et al. "Deacylative Condensation I."
Chemistry Letters 47 (1979) Y. Ueno et al.
Neumann et al., Jour. Amer. Chem. Soc. vol. 77, (1955), p. 5676.

Primary Examiner—Elbert L. Roberts
Attorney, Agent, or Firm—Bruce Stein

[57] ABSTRACT

A process is disclosed for the production of 17-keto-16-methylene steroids (III) from the corresponding readily available 17-keto steroid (I) via a novel intermediate (II).

28 Claims, No Drawings

PROCESS FOR PREPARING 16-METHYLENE STEROIDS

DESCRIPTION

BACKGROUND OF THE INVENTION

16-Methylene steroids are well known chemically in the estrone (aromatic A ring) series, see U.S. Pat. No. 3,257,429; in the corticoid series, see U.S. Pat. Nos. 3,157,679, 3,878,228, 3,354,184, 3,493,558 and 3,376,294; in the progesterone series, see U.S. Pat. Nos. 3,168,537, 3,157,679, 3,284,476 and 3,359,287; and in the androstane series, see U.S. Pat. Nos. 3,641,069 and 3,300,521.

Pharmacologically, the 16-methylene steroids are known to be useful as anti-inflammatory agents, see U.S. Pat. Nos. 3,641,069, 3,878,228 and 3,359,287; as progestational agents, see U.S. Pat. Nos. 3,157,679, 3,168,537, 3,284,476, 3,359,287 and 3,493,558; as estrogen hormonal agents, see U.S. Pat. Nos. 3,257,429 and 3,284,476; and as intermediates, see U.S. Pat. Nos. 3,300,521 and 3,354,184.

While there is more than one process to produce 16-methylene steroids, the most common process is the transformation of a 16-unsaturated-16-methyl steroid to the corresponding 16-methyl-16α,17α-epoxide followed by conversion to the corresponding 17α-hydroxy-16-methylene steroid, see U.S. Pat. Nos. 3,168,537, 3,354,184, 3,539,287, 3,493,558, 3,376,294 and 3,284,476. In addition, there is a process for the conversion of 17-keto steroids (I) to the corresponding 16-methylene steroid (III) by reacting the 17-keto steroid with formaldehyde (paraformaldehyde) and an amine followed by elimination of the amine, see U.S. Pat. Nos. 3,704,253 and 3,275,666. The process of the present invention first selectively activates the $C_{16}$ position before reaction with formaldehyde and a base.

Y. Ueno et al. in Tetrahedron Letters 3753 (1978) described a process for reacting monosubstituted active methylene compounds (β-ketoesters) with paraformaldehyde and base to produce α-methylenated esters. When cyclopentanone was the ketone portion of the β-keto ester, α-methylenation occurred; however the yield was only 53%, and, more importantly, the product was not an α-methylenated cyclopentanone because ring opening occurred forming a substituted pentanoic acid.

Y. Ueno et al. in Chemistry Letters 47 (1979) applied the same method to α-monosubstituted β-benzoylsulfones and obtained α-methylenated sulfones.

Processes are known for the production of various substituted 16-methylene steroids, see U.S. Pat. Nos. 3,641,069 and 3,376,294 (6-fluoro), 3,878,228 (9-fluoro), 3,157,679 (6α-methyl), and 3,300,521 (7-methyl).

Hungarian patent 019,495 discloses a process for transforming a 16-substituted (16-alkoxalyl) steroid to the corresponding 16-methylene steroid in 80–90% yield by reaction with aqueous formaldehyde in the presence of a nitrogen containing organic base such as triethylamine or pyridine which was used as the solvent.

P. DeRuggieri et al. in Gazzetter Chim. Ital. 91, 672 (1961) described a procedure to transform a 17-keto steroid to the corresponding 16-methylene steroid by utilizing a Mannich reaction, not a 16-(alkyloxalyl) intermediate. DeRuggieri does produce a 16-(ethyloxalyl)-17-keto steroid intermediate but does not convert it to a 16-methylene steroid but rather forms a 16-methyl-16-(ethyloxalyl)-17-keto steroid intermediate which is transformed to a 16β-methyl steroid, not a 16-methylene steroid.

BRIEF DESCRIPTION OF THE INVENTION

Disclosed is the 16-substituted steroid (IIB).

Also disclosed are the 16-methylene steroids (IIIA and IIIB).

Disclosed is a process to prepare a 16-methylene steroid (III) and $C_3$ protected forms thereof which comprises starting with the corresponding 17-keto steroid (I) and $C_3$ protected forms thereof and (1) contacting the 17-keto steroid (I) with a $C_{16}$-activating agent in the presence of an enolizing base to produce the corresponding 16-substituted steroid (II) and $C_3$ protected forms thereof and (2) contacting the reaction mixture of Step 1 with a formaldehyde generating agent.

Disclosed is a process to prepare a 16-methylene steroid (III) and $C_3$ protected forms thereof which comprises starting with the corresponding 16-substituted steroid (II) and $C_3$ protected forms thereof and contacting the 16-substituted steroid (II) with a formaldehyde generating agent in the presence of a base.

DETAILED DESCRIPTION OF THE INVENTION

The 17-keto steroid (IA–ID) starting materials are well known to those skilled in the art or can be readily prepared from known compounds by methods well known to those skilled in the art.

The D ring of the 17-keto steroids (I–III) is the same, regardless of the substitution of rings A, B and C, see Chart A for formulas ((I–III). Various combinations of A, B and C rings are covered, see Chart B for formulas (A–D).

Considered as equivalent of the A ring functionalities of (IA–ID and IIA–IID) are the $C_3$ protected forms as is well known to those skilled in the art. The $C_3$ protected forms are readily interconvertible and interchangeable with the $C_3$ non-protected forms. These include, for example, the enol ethers, enol esters, ethers, ketals, enamines, esters, oximes, etc. With the $\Delta^{1,4}$-3-keto functionality (B) it is not necessary to protect the 3-ketone.

The preferred ethers are methyl and ethyl and the preferred esters are acetate and benzoate. For example, the process of Examples 1 and 2 was performed on the 3-enol ether of a $\Delta^4$-3-keto steroid (A) which can be readily converted or transformed to the $\Delta^4$-3-keto functionality (A).

It is preferred that the A-B ring saturation/unsaturation be $\Delta^4$-3-keto (A), or $\Delta^{1,4}$-3-keto (B) and $C_3$ protected forms thereof.

Various substitutions at $C_6$, $C_9$ and $C_{11}$ are well known to those skilled in the art. The preferred C-ring substitution is a saturated C ring ($R_9$ and $R_{11}$ are both hydrogen atoms) or the $\Delta^{9(11)}$ functionality ($R_9$ and $R_{11}$ are both nothing). Also included and considered equivalent of the $\Delta^{9(11)}$ functionality is the 9β,11β-epoxide. This is because the $\Delta^{9(11)}$ functionality can be readily transformed by methods well known to those skilled in the art to the corresponding 9β,11β-epoxide which in turn can be transformed in one step to the corresponding 9α-fluoro-11β-hydroxy functionality ($R_9$ is a fluorine atom and $R_{11}$ is a β-hydroxy group).

The process of the present invention involve transformation or conversion of a 17-keto steroid (I) to a 16-methylene steroid (III) via a 16-substituted steroid intermediate (II). The process can be performed two ways: (1) with isolation of the 16-substituted intermediate (II), and (2) without isolation of the 16-substituted intermediate (II). In the first case, the 17-keto steroid (I) is reacted with the $C_{16}$ activating agent in the presence of a strong base, the intermediate (II) is isolated and reacted with a formaldehyde generating agent in the presence of a base. In the second case, after the 16-substituted intermediate (II) is generated, the formaldehyde generating agent is added without additional base. These two processes are considered the equivalent of each other.

The 17-keto steroid (IA–ID), or as the $C_3$ protected form, is reacted with a $C_{16}$ activating agent in the presence of an enolizing base. The $C_{16}$ activating agent is a compound which when reacted with a 17-keto steroid (I) and an enolizing base activates the $C_{16}$ position of the 17-keto steroid (I) so as to make it reactive to the addition of formaldehyde. $C_{16}$ activating agents include compounds of the formula X—CO—R where R is a hydrogen atom or an electron withdrawing group such as a trifluoromethyl group, cyano group or $COOR_{16}$. The leaving group, X, is $OR_b$, chlorine, bromine or iodine. It is preferred that the $C_{16}$ activating group is selected from the group consisting of oxylal esters (such as methyl and ethyl oxylate), formyl esters (such as methyl or ethyl formate), trifluoroacetate esters (such as methyl or ethyl trifluoroacetate).

The enolizing base is a base sufficiently strong to form an enolate at $C_{17}$ and in conjunction with a $C_{16}$ activating agent form a 16-substituted intermediate (II). Generally the enolizing base is a strong base which has a pK of greater than 12. It is preferred that the enolizing base be selected from the group consisting of metal-ORb, metal hydride, or metal amides. Metal refers to lithium, sodium, potassium or magnesium, and Rb is alkyl of 1 thru 5 carbon atoms or phenyl. Enolizing bases include, for example, sodium methoxide, potassium ethoxide, sodium hydride, or lithium diisopropylamide. It is preferred that the metal is sodium and the base is sodium methoxide or sodium ethoxide. The reaction should be performed in an inert solvent, preferably selected from solvents such as toluene, methylene chloride, THF, but may also be performed in alcohols such as methanol, ethanol, etc. The reaction should be performed under an inert atmosphere, preferably nitrogen, in a temperature range of $-20°$ to $50°$.

The reaction is monitored by TLC as is well known to those skilled in the art. When the reaction is complete, the 16-substituted steroid (IIA–IID) can be isolated (Example 1) or can be reacted in situ (Example 3 and 4) to produce the desired 16-methylene steroid (III).

In either event, formaldehyde or a formaldehyde generating agent is then added.

Before the formaldehyde generating agent is added, it is important to neutralize all the excess enolizing base. This is preferably done by the addition of an acid such as acetic acid (Examples 7–10) or hydrochloric acid (Example 1). A formaldehyde generating agent is a compound which, when used or reacted, acts as, or generates formaldehyde (HCHO) so that the formaldehyde generating agent could be formaldehyde itself or a compound or polymer which produces formaldehyde in situ or acts as formaldehyde. It is preferred that the formaldehyde generating agent be selected from the group consisting of formaldehyde, paraformaldehyde, trioxane and an aqueous or alcoholic solution of formaldehyde. It is more preferred that the formaldehyde generating agent be paraformaldehyde or an aqueous solution of formaldehyde. In the event that the 16-substituted steroid (II) is not isolated and the reaction is being performed as a one-pot process, the reaction mixture is sufficiently basic to cause the transformation of the 16-substituted steroid (II) to the 16-methylene steroid (III). If the reaction is being performed as a two-pot process with isolation of the 16-substituted steroid (II) intermediate, the second step requires that a base be added. There may be a strong base such as $OR_b$ or a weak base such as tertiary amines. Preferred weak bases include, for example, triethylamine, tributylamine, or pyridine. Triethylamine is the preferred weak base. The reaction should be performed in an inert solvent such as the first step. The weak base can serve as solvent or cosolvent. The reaction is performed under an inert atmosphere, preferably nitrogen, in a temperature range of $0°$ to reflux. The reaction is monitored by TLC as is well known to those skilled in the art and is complete in 0.25 to 6 hr, usually about 1 hr, depending on temperature, etc. When complete, the 16-methylene steroid (III) is isolated and purified by means well known to those skilled in the art.

If the 16-methylene steroid (III) is obtained in a $C_3$ protected form, the $C_3$ protecting group is readily removable and the A ring functionality is readily convertible to formulas (A–D) by means well known to those skilled in the art.

The 16-methylene steroids (III) are useful as intermediates to produce other pharmacologically useful steroids.

For example, the 16-methylene steroid (III) can be transformed to the corresponding 17-keto-16β-methyl steroid by the hydrogenation process of U.S. Pat. No. 3,704,253, Example 3. This 17-keto-16β-methyl steroid can then be transformed to the corresponding 16β-methyl corticoid by the process of U.S. Pat. No. 4,041,055 and other known steroid chemistry. Therefore, starting with the appropriate 17-keto steroid (I), one could produce betamethasone, a commercially important anti-inflammatory agent.

DEFINITIONS

The definitions and explanations below are for the terms as used throughout the entire patent application including both the specification and claims.

All temperatures are in degrees Centigrade.

TLC refers to thin-layer chromatography.

THF refers to tetrahydrofuran.

Saline refers to an aqueous saturated sodium chloride solution.

NMR refers to nuclear (proton) magnetic resonance spectroscopy, chemical shifts are reported in ppm (δ) downfield from TMS.

TMS refers to tetramethylsilane.

When solvent pairs are used, the ratio of solvents used are volume/volume (v/v).

R is a hydrogen atom, trifluoromethyl or cyano group or $COOR_{16}$.

$R_3$ is —$OR_b$, —$OCOR_b$ or —$N(R_b)_2$ with the provisos that (1) with $N(R_b)_2$, both $R_b$'s cannot be phenyl and (2) when $R_3'$ is $OR_b$, $R_3$ is $OR_b$ and the $R_b$'s can be connected to form a ring of 5 or 6 atoms.

$R_3'$ is a hydrogen atom, nothing or —$OR_b$ with the proviso that when $R_3'$ is $OR_3$ is $OR_b$ and the $R_b$'s can be connected to form a ring of 5 or 6 atoms.

$R_6$ is a hydrogen or fluorine atom or methyl group.

$R_9$ is nothing or a hydrogen or fluorine atom, which includes the $\Delta^{9(11)}$ and $9\beta,11\beta$-epoxide functionality.

$R_{10}$ is a hydrogen atom or methyl group.

$R_{11}$ is nothing or a hydrogen or oxygen atom, an $\alpha$-hydroxy group, or a $\beta$-hydroxy group, which includes the $\Delta^{9(11)}$ and $9\beta,11\beta$-epoxide functionality.

$R_{16}$ is alkyl of 1 thru 3 carbon atoms.

.... is a single or double bond.

~ indicates that the attached group can be in either the $\alpha$ or $\beta$ configuration.

Metal refers to lithium, sodium, potassium or magnesium.

When the term "alkyl of __ thru __ carbon atoms" is used, it means and includes isomers thereof where such exist.

X is $OR_b$, chlorine, bromine, or iodine.

$R_b$ is alkyl of 1 thru 5 carbon atoms or phenyl.

A formaldehyde generating agent is a compound which, when used or reacted, acts as, or generates, formaldehyde (HCHO) so that the formaldehyde generating agent could be formaldehyde itself or a compound which produces formaldehyde in situ or acts as formaldehyde.

$C_{16}$ activating agent is a compound which, when reacted with a 17-keto steroid (I) and an enolizing base produces a 16-substituted intermediate (II) and activates the $C_{16}$ position of the 17-keto steroid (I) so as to make it reactive to the addition of formaldehyde.

An enolizing base is a base which when reacted with a 17-keto steroid (I) and a $C_{16}$ activating agent produces a 16-substituted intermediate (II).

A $C_3$ protecting group is a group ($R_3$ and $R_3'$) which protects the $C_3$ ketone of compounds of formulas (A and B) and/or the $C_3$ hydroxyl of compounds of formulas (C and D) where the $C_3$ protected forms of formulas (A-D) can be represented by the formulas (A'-C')

(D')

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants as well as reaction conditions and techniques.

Example 1

3-Methoxy-16-(methyloxalyl)androsta-3,5,9(11)-trien-17-one (II)

Dimethyloxalate (11.5 g) and sodium methoxide (6.5 g) was added to a mixture of 3-methoxyandrosta-3,5,9(11)-trien-17-one (I, U.S. Pat. No. 3,516,991, 17 g) and toluene (100 ml). This mixture was stirred overnight at 20°-25° under nitrogen during which time a precipitate occurred. Water, saline, methanol, and potassium hydroxide (5%) were added and, following separation of the layers, the organic layer was further washed with potassium hydroxide (5%). The aqueous layers were combined and neutralized to pH of 5 with hydrochloric acid (2 N) and extracted twice with methylene chloride. The organic layers were combined and dried over sodium sulfate, filtered and the filtrate concentrated under reduced pressure to an oil which is crystallized from methanol to give the title compound.

NMR (CDCl$_3$)=0.99, 1.19, 3.18, 3.60, 3.89, 5.20, 5.30 and 5.54 $\delta$.

Example 2

3-Methoxy-16-methyleneandrosta-3,5,9(11)-trien-17-one (III)

To a mixture of 3-methoxy-16-(methyloxalyl)androsta-3,5,9(11)-trien-17-one (II, Example 1, 13.9 g) in THF (125 ml) was added paraformaldehyde (1.62 g) and triethylamine (7.5 ml). The resulting mixture was refluxed for one hour at which time TLC (ethyl acetate/toluene: 1/9) showed the reaction to be complete. The reaction mixture was poured into an aqueous salt solution and extracted with ethyl acetate. The organic phase was dried over sodium sulfate, filtered and concentrated under reduced pressure to give an oily residue which was crystallized from methanol to give the title compound.

NMR (CDCl$_3$)=0.90, 1.13, 3.57, 5.17, 5.30, 5.40, 5.56 and 6.08 $\delta$.

Example 3

16-(Methyloxalyl)androsta-1,4,9(11)-triene-3,17-dione (II)

A 25% solution of sodium methoxide in methanol (0.252 ml) was added to a mixture of androsta-1,4,9(11)-triene-3,17-dione (I, U.S. Pat. No. 4,216,159, Preparation 4, 282 mg), dimethyloxalate (175 mg) and methylene chloride (3 ml) at 0°. This mixture was stirred at 0° for 4.5 hrs, following which an additional 0.03 ml of methoxide solution was added, and the stirring was continued for an additional two hours. At this time, conversion to the title compound was essentially complete as measured by TLC (acetone/methylene chloride; 5/95).

Example 4

16-Methyleneandrosta-1,4,9(11)-triene-3,17-dione (III)

Sodium bicarbonate (16 mg), paraformaldehyde (45 mg), THF (2 ml) and triethylamine (0.1 ml) were added to 16-(methyloxalyl)androsta-1,4,9(11)-triene-3,17-dione (II, Example 3, reaction mixture) and on stirring for one hour at 0°, the conversion to the title compound was complete as measured by TLC. The reaction mixture was poured into pH 7 buffer and the mixture was extracted with ethyl acetate. The organic extract was washed with water, dried over sodium sulfate, filtered and the filtrate concentrated under reduced pressure to give the title compound.

NMR (CDCl$_3$)=0.90, 1.44, 3.87, 5.40, 5.58, 6.03, 6.21 and 7.21 δ.

Example 5

3-Methoxy-16-methyleneandrosta-3,5,9(11)-trien-17-one (III)

3-Methoxy-16-(methyloxalyl)androsta-3,5,9(11)-triene-17-one (II, Example 1, 385 mg) was refluxed with paraformaldehyde (45 mg), triethylamine (0.2 ml) and THF (4 ml) and then allowed to stand at 20°–25° for 48 hr. The reaction mixture was extracted with ethyl acetate-water, the organic layer was dried and concentrated under reduced pressure to give the title compound.

Example 6

3-Methoxy-16-methyleneandrosta-3,5,9(11)-trien-17-one (III)

3-Methoxy-16-(methyloxyalyl)androsta-3,5,9(11)-trien-17-one (II, Example 1, 10 g) in THF (100 ml) and paraformaldehyde (1.17 g) and triethylamine (5.4 ml) were refluxed for 1 hr under nitrogen. The reaction mixture should be extracted, preferably with ethyl acetate/water and not methylene chloride/water which produces an emulsion. Upon workup, the title compound is obtained.

Example 7

3-Methoxy-16-methyleneandrosta-3,5,9(11)-trien-17-one (III)

3-Methoxyandrosta-3,5,9(11)-trien-17-one (I, 20 g) in THF (220 ml) was combined with dimethyloxylate (11.8 g) and sodium methoxide (25%, 18.4 ml) at 0° under nitrogen. After the reactants were combined, the ice was removed. After one hour, TLC shows the reaction has gone cleanly. Triethylamine (7.0 ml), acetic acid (1.0 ml), paraformaldehyde (3 g), and methanol (28 ml) were added and the mixture stirred overnight at 20°–25°. TLC showed the reaction had gone to completion. The reaction mixture was washed with phosphate buffer (121 ml) and water (202 ml). The mixture was extracted with methylene chloride (48 ml) and again with methylene chloride (40 ml). The methylene chloride extracts were combined and back-extracted with water (80 ml) and saline (10 ml). The organic mixture was concentrated under reduced pressure to give the title compound.

Example 8

3-Methoxy-16-methyleneandrosta-3,5-dien-17-one (III)

3-Methoxyandrosta-3,5-diene-17-one (I, 2.0 g) was mixed with THF (22 ml). Diethyloxylate (1.45 ml) was added and the mixture cooled in an ice bath. Sodium methoxide (25%, 1.83 ml) was added dropwise with stirring. The mixture was stirred, and after removing the ice bath for one hour TLC showed the reaction to be complete. The reaction mixture was cooled in an ice bath, acetic acid (0.1 ml) was added, followed by triethylamine (0.7 ml) and methanol (2.8 ml). Formaldehyde (37%, 0.3 g) was added and the mixture stirred for 40 min. Then formaldehyde (37% aqueous, 0.61 g) was added and the mixture stirred at 20°–25° for about 45 minutes. TLC showed the reaction to be done. Water (10 ml) and ethyl acetate (10 ml) were added and the mixture stored at about −20° overnight. The mixture was warmed, the layers are separated, and the organic layer was washed twice with saline. The aqueous layer was extracted with ethyl acetate, the ethyl acetate washed with saline, and the organic extracts combined and dried over sodium sulfate, filtered and concentrated under reduced pressure to give the title compound.

Example 9

16-Methyleneandrosta-1,4,9(11)-triene-3,17-dione (III)

Androsta-1,4,9(11)-triene-3,17-dione (I, 0.7 g) in THF (8 ml) and dimethyloxylate (0.44 g) were combined and cooled to 3° in an ice bath. Sodium methoxide in methanol (25%, 0.685 ml) was added dropwise with no temperature rise. TLC after about ½ hr showed the reaction was nearly completed. Acetic acid (0.05 ml), triethylamine (0.26 ml) and methanol (1 ml) were added. Formaldehyde (37%, 0.28 ml) was added and the reaction mixture stirred at 20°–25°. TLC, after approximately 1½ hrs, showed the reaction was complete. The reaction mixture was added to water and extracted with ethyl acetate. The layers were separated, the aqueous layer was extracted with ethyl acetate and combined with the organic extract. The combined organic extract was washed with water and separated from the organic layer. Methylene chloride was added and the mixture dried over sodium sulfate. The mixture was filtered and the filtrate was concentrated under reduced pressure to an oil. Acetone was added and the title compound was obtained upon crystallization.

Example 10

6-Methyl-16-methyleneandrosta-4,6-diene-3,17-dione (III)

6-Methylandrosta-4,6-diene-3,17-dione (I, 3.0 g) was dissolved in THF (32 ml) and dimethyloxalate (1.64 g) was added. The mixture was cooled under nitrogen to 0°. Sodium methoxide in methanol (25%, 2.75 ml) was added dropwise. The mixture was stirred approximately 2 hrs. at 0°; then neutralized with acetic acid (0.12 ml). Triethylamine (1.2 ml) and methanol (5.0 ml) were added followed by formaldehyde solution (37%, 1.13 ml). Following addition of all the reactants, the ice bath was removed and the reaction stirred at 20°–25° for 1.5 hrs. Water (50 ml) was added, followed by ethyl acetate and methyl t-butyl ether. These phases were separated and the organic phase was washed twice with saline. The combined aqueous layers were back extracted once with ethyl acetate and the combined organic extracts were dried over sodium sulfate after the addition of some methylene chloride. The mixture was filtered through Celite and the filtrate removed under reduced pressure to give an oil which was chromatographed over silica gel (230–400 mesh, 140 g). The appropriate fractions were pooled and concentrated to give the title compound.

CHART A

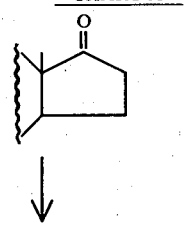

(I)

-continued

CHART A

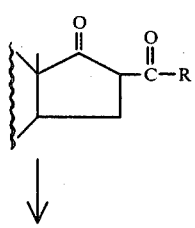

↓

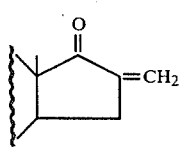

CHART B (A)
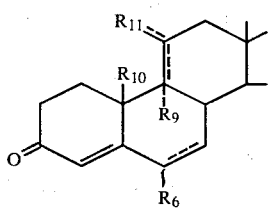

(B)
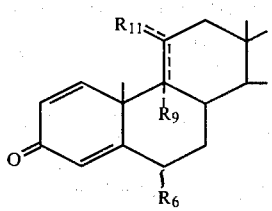

(C)
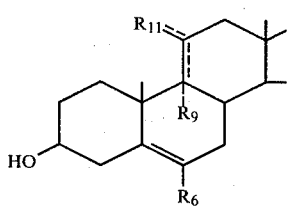

(D)
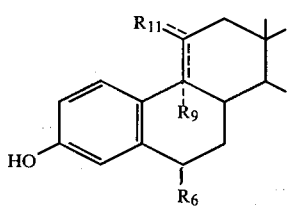

What is claimed is:

1. A 16-substituted steroide of the formula

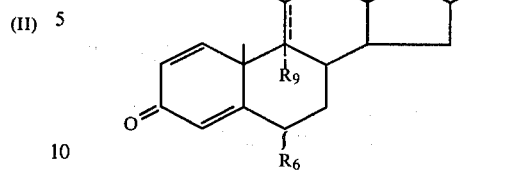

where
- R is a hydrogen atom, trifluoromethyl or cyano group or $COOR_{16}$,
- $R_6$ is a hydrogen or fluorine atom or methyl group,
- $R_9$ is nothing or a hydrogen or fluorine atom, which includes the $\Delta^{9(11)}$ and $9\beta,11\beta$-epoxide functionality,
- $R_{11}$ is nothing or a hydrogen or oxygen atom, an $\alpha$-hydroxy group, or a $\beta$-hydroxy group, which includes the $\Delta^{9(11)}$ and $9\beta,11\beta$-epoxide functionality,
- ⋯ is a single or double bond, and
- ~ indicates that the attached group can be in either the $\alpha$ or $\beta$ configuration.

2. A compound according to claim 1 where $R_9$ and $R_{11}$ are hydrogen atoms, and the ⋯ in the C ring is a single bond, or where $R_9$ and $R_{11}$ are nothing and ⋯ in the C ring is a double bond.

3. A compound according to claim 1 where R is —COOCH$_3$.

4. A compound according to claim 1 where R is —COOC$_2$H$_5$.

5. A compound according to claim 1 which is 16-(methyloxalyl)androsta-1,4,9(11)-triene-3,17-dione.

6. A 16-methylene steroid of the formula

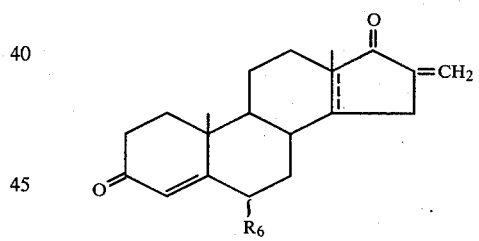

and C$_3$ protected forms thereof where $R_{10}$ is a hydrogen atom or methyl group and where $R_6$, $R_9$, $R_{11}$, ⋯ and ~ are defined in claim 1.

7. A 16-methylene steroid according to claim 6 which is 3-methoxy-16-methyleneandrosta-3,5,9(11)-trien-17-one.

8. A 16-methylene steroid according to claim 6 which is 3-methoxy-16-methyleneandrosta-3,5-dien-17-one.

9. A 16-methylene steroid of the formula

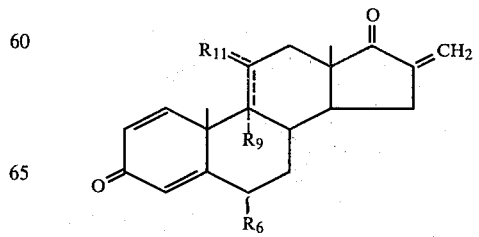

where $R_6$, $R_9$, $R_{11}$, ⋯ and ∼ are defined in claim 1.

10. A 16-methylene steroid according to claim 9 where $R_9$ and $R_{11}$ are hydrogen atoms, and the ⋯ in the C ring is a single bond, or where $R_9$ and $R_{11}$ are nothing and ⋯ in the C ring is a double bond.

11. A 16-methylene steroid according to claim 9 which is 16-methyleneandrosta-1,4,9(11)-triene-3,17-dione.

12. A process to prepare a 16-methylene steroid of the formula

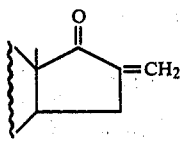
(III)

and $C_3$ protected forms thereof which comprises starting with the corresponding 17-keto steroid

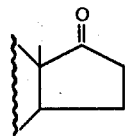
(I)

and $C_3$ protected forms thereof, and
(1) containing the 17-keto steroid (I) with a $C_{16}$-activating agent in the presence of an enolizing base to produce the corresponding 16-substituted steroid of the formula

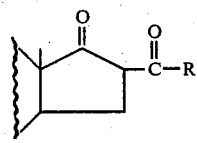
(II)

and $C_3$ protected forms thereof; and
(2) contacting the reaction mixture of Step 1 with a formaldehyde generating agent where R is a hydrogen atom, trifluoromethyl or cyano group or $COOR_{16}$ where $R_{16}$ is alkyl of one through 3 carbon atoms.

13. A process according to claim 12 where the 17-keto steroid (I) is selected from the group consisting of

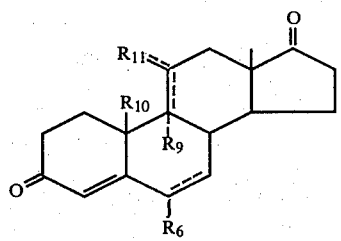
(IA)

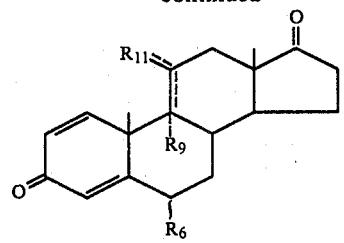
(IB)

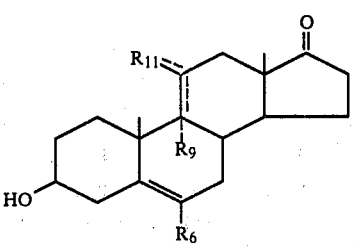
(IC)

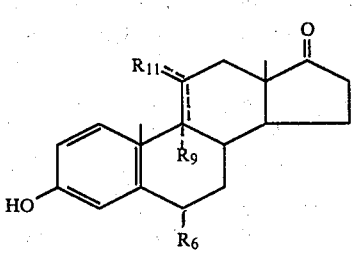
(ID)

and $C_3$ protected forms of IA, IC and ID where $R_6$, $R_9$, $R_{11}$, ⋯ and ∼ are defined in claim 1, and where $R_{10}$ is defined in claim 6.

14. A process according to claim 12 where the 16-methylene steroid (III) is selected from the group consisting of

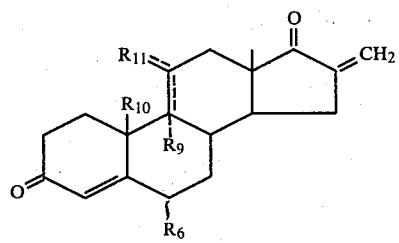
(IIIA)

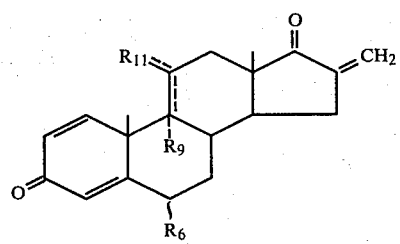
(IIIB)

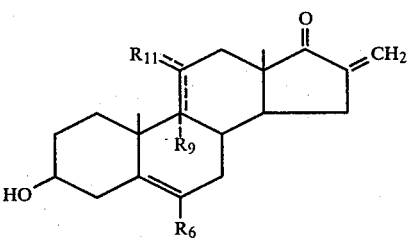
(IIIC)

-continued

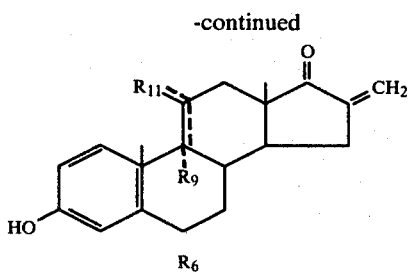

and C₃ protected forms of IIIA, IIIC and IIID where $R_6$, $R_9$, $R_{11}$, ⁓ and ⁓ are defined in claim 1, and where $R_{10}$ is defined in claim 6.

15. A process according to claim 14 where the 16-methylene steroid (IIIA) is selected from the group consisting of 3-methoxy-16-methyleneandrosta-3,5,9(11)-trien-17-one, 3-methoxy-16-methyleneandrosta-3,5-dien-17-one and 6-methyl-16-methyleneandrosta-4,6-diene-3,17-dione.

16. A process according to claim 14 where the 16-methylene steroid (IIIB) is 16-methyleneandrosta-1,4,9(11)-triene-3,17-dione.

17. A process according to claim 12 where the $C_{16}$ activating agent is selected from the group consisting of X—CO—R, where R, and X are defined in the specification.

18. A process according to claim 17 where the $C_{16}$ activating agent is X—CO—COOR₁₆ where $R_{16}$ is defined in the specification.

19. A process according to claim 12 where the enolizing base is selected from the group consisting of metal-OR_b, a metal hydride or metal amide, where metal and $R_b$ are defined in the specification.

20. A process according to claim 19 where the enolizing base is sodium methoxide or sodium ethoxide.

21. A process according to claim 12 where the formaldehyde generating agent is selected from the group consisting of formaldehyde, paraformaldehyde, trioxane, and an aqueous or alcoholic solution of formaldehyde.

22. A process according to claim 21 where the formaldehyde generating agent is paraformaldehyde or an aqueous solution of formaldehyde.

23. A process to prepare a 16-methylene steroid of the formula

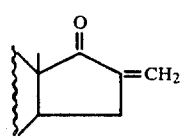

and C₃ protected forms thereof, which comprises starting with the corresponding 16-substituted steroid of the formula

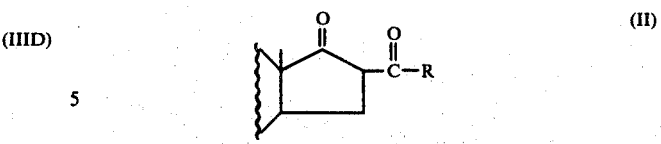

and C₃ protected forms thereof and contacting the 16-substituted steroid (II) with a formaldehyde generating agent in the presence of a base where R is defined in claim 1.

24. A process according to claim 23, where the 16-methylene steroid (III) is selected from the group consisting of

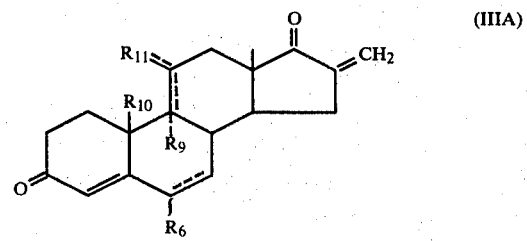

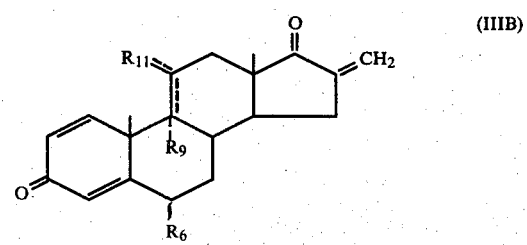

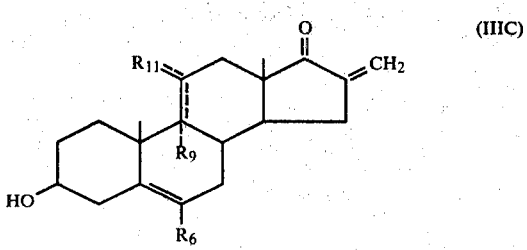

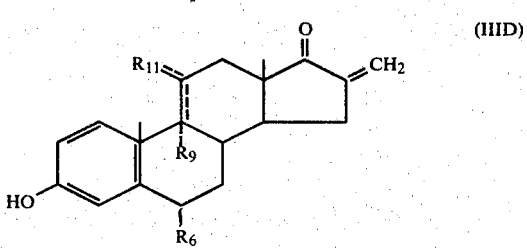

and C₃-protected forms thereof and where $R_6$, $R_9$, $R_{11}$, ⁓ ⁓ ⁓ and ⁓ are defined in claim 1 and where $R_{10}$ is defined in claim 6.

25. A process according to claim 23 where the formaldehyde generating agent is selected from the group consisting of formaldehyde, paraformaldehyde, trioxane and an aqueous or alcoholic solution of formaldehyde.

26. A process according to claim 25 where the formaldehyde generating agent is selected from the group consisting of paraformaldehyde or an aqueous solution of formaldehyde.

27. A process according to claim 23 where the weak base is selected from the group consisting of OR_b, triethylamine, tributylamine, or pyridine.

28. 3-Methoxy-16-(methyloxalyl)androsta-3,5,9(11)-trien-17-one.

* * * * *

UNITED STATES PATENT OFFICE
CERTIFICATE OF CORRECTION

Patent No. 4,416,821        Dated November 22, 1983

Inventor(s) Verlan H. VanRheenen

It is certified that error appears in the above-identified patent and that said Letters Patent are hereby corrected as shown below:

Column 4, line 66, "when $R_3'$ is $OR_3$ is $OR_b$ and" should read
--when $R_3'$ is $OR_b$, $R_3$ is $OR_b$ and--.

Column 5, line 47, "$R'_3$" should read --$R_3'$--

Column 7, line 54, "3,5-diene-17-one" should read --3,5-dien-17-one--

Column 10, line 40 (IIIA'), should appear as follows instead of as in the patent:

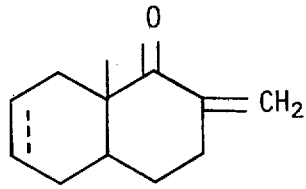

Column 13, line 14, "$R_{11}$, and ∿ are" should read --$R_{11}$, .... and ∿ are--

Signed and Sealed this

Third Day of April 1984

[SEAL]

Attest:

Attesting Officer

GERALD J. MOSSINGHOFF

*Commissioner of Patents and Trademarks*